(12) United States Patent
Cotteret

(10) Patent No.: US 7,951,209 B2
(45) Date of Patent: May 31, 2011

(54) COMPOSITION FOR THE OXIDATION DYEING OF KERATIN FIBRES, COMPRISING AT LEAST ONE 4,5- OR 3,4-DIAMINOPYRAZOLE OR A TRIAMINOPYRAZOLE AND AT LEAST ONE SELECTED CARBONYL COMPOUND, AND DYEING PROCESS

(75) Inventor: Jean Cotteret, Verneuil sur Seine (FR)

(73) Assignee: L'Oreal (FR)

( * ) Notice: Subject to any disclaimer, the term of this patent is extended or adjusted under 35 U.S.C. 154(b) by 0 days.

(21) Appl. No.: 11/975,995

(22) Filed: Oct. 23, 2007

(65) Prior Publication Data

US 2008/0141468 A1 Jun. 19, 2008

Related U.S. Application Data

(63) Continuation of application No. 10/451,553, filed as application No. PCT/FR01/03729 on Nov. 26, 2001, now abandoned.

(30) Foreign Application Priority Data

Dec. 22, 2000 (FR) .................................. 00 16952

(51) Int. Cl.
*A61K 8/49* (2006.01)
(52) U.S. Cl. ............. 8/409; 8/405; 8/406; 8/408; 8/416; 8/429
(58) Field of Classification Search ............. 8/408, 409, 8/416, 428, 429, 405, 406
See application file for complete search history.

(56) References Cited

U.S. PATENT DOCUMENTS

| | | | | |
|---|---|---|---|---|
| 3,415,608 A | * | 12/1968 | Tucker | ............................. 8/416 |
| 4,932,977 A | | 6/1990 | Schultz | |
| 5,034,014 A | | 7/1991 | Wenke | |
| 5,061,289 A | | 10/1991 | Clausen et al. | |
| 5,663,366 A | | 9/1997 | Neunhoeffer et al. | |
| 5,718,731 A | | 2/1998 | Loewe et al. | |
| 5,766,576 A | | 6/1998 | Lowe et al. | |
| 5,865,855 A | | 2/1999 | Doehling et al. | |
| 6,001,135 A | * | 12/1999 | Rondeau et al. | ................... 8/407 |
| 6,099,592 A | | 8/2000 | Vidal et al. | |
| 6,254,646 B1 | * | 7/2001 | Di La Mettrie et al. | .......... 8/406 |
| 6,303,794 B1 | * | 10/2001 | Guth et al. | ..................... 548/547 |
| 6,312,479 B1 | * | 11/2001 | Maubru | ............................ 8/407 |
| 6,357,330 B1 | * | 3/2002 | Dass et al. | ...................... 83/863 |
| 6,537,330 B1 | | 3/2003 | Hoeffkes et al. | |
| 2001/0049849 A1 | | 12/2001 | Mettrie et al. | |
| 2002/0035758 A1 | | 3/2002 | Pratt | |

FOREIGN PATENT DOCUMENTS

| | | | |
|---|---|---|---|
| DE | 38 43 892 A1 | | 6/1990 |
| DE | 42 34 886 A1 | | 4/1994 |
| DE | 19810887 A1 | | 9/1999 |
| EP | 375977 A1 | | 7/1990 |
| EP | 0 749 748 A1 | | 12/1996 |
| EP | 0 873 745 A2 | | 10/1998 |
| EP | 1345580 A1 | | 9/2003 |
| JP | 60-028912 | | 2/1985 |
| WO | 90/07504 | | 7/1990 |
| WO | 94/08969 | * | 4/1994 |
| WO | 9609807 A1 | | 4/1996 |
| WO | 9735553 A1 | | 10/1997 |
| WO | 98/22078 A1 | | 5/1998 |
| WO | 9852523 A1 | | 11/1998 |
| WO | 9911231 A1 | | 3/1999 |
| WO | 99/17722 | * | 4/1999 |
| WO | 99/17731 | * | 4/1999 |
| WO | 00/33799 | | 6/2000 |
| WO | 00/38640 A1 | | 7/2000 |
| WO | 0038633 A1 | | 7/2000 |
| WO | 0061087 A1 | | 10/2000 |
| WO | 0147483 A1 | | 7/2001 |
| WO | 01/70182 | | 9/2001 |
| WO | 01/85111 A1 | | 11/2001 |
| WO | 02/22092 A1 | | 3/2002 |
| WO | 02051373 A1 | | 7/2002 |

* cited by examiner

*Primary Examiner* — Lorna M Douyon
*Assistant Examiner* — Amina Khan
(74) *Attorney, Agent, or Firm* — Lerner, David, Littenberg, Krumholz & Mentlink, LLP

(57) ABSTRACT

The present invention relates to a composition for the oxidation dyeing of keratin fibres, in particular of human keratin fibres such as the hair, comprising at least one oxidation base chosen from 4,5- or 3,4-diaminopyrazoles and triaminopyrazoles, in combination with at least one selected carbonyl compound, and also to the dyeing process using this composition with an oxidizing agent.

23 Claims, No Drawings

COMPOSITION FOR THE OXIDATION DYEING OF KERATIN FIBRES, COMPRISING AT LEAST ONE 4,5- OR 3,4-DIAMINOPYRAZOLE OR A TRIAMINOPYRAZOLE AND AT LEAST ONE SELECTED CARBONYL COMPOUND, AND DYEING PROCESS

The present invention relates to a composition for the oxidation dyeing of keratin fibres, in particular of human keratin fibres such as the hair, comprising at least one oxidation base chosen from 4,5- or 3,4-diaminopyrazoles and triaminopyrazoles, in combination with at least one selected carbonyl compound, and also to the dyeing process using this composition with an oxidizing agent.

It is known practice to dye keratin fibres, and in particular human hair, with dye compositions containing oxidation dye precursors, in particular ortho- or para-phenylenediamines, ortho- or para-aminophenols or heterocyclic compounds such as pyrazole derivatives which are generally referred to as oxidation bases. Oxidation dye precursors, or oxidation bases, are colourless or weakly coloured compounds which, when combined with oxidizing products, can give rise to coloured compounds and dyes by a process of oxidative condensation.

It is also known that the shades obtained with these oxidation bases can be varied by combining them with suitably selected couplers or coloration modifiers, the latter being chosen in particular from aromatic meta-diamines, meta-aminophenols, meta-diphenols and certain heterocyclic compounds.

The variety of molecules used as regards the oxidation bases and the couplers allows a wide range of colours to be obtained.

The "permanent" coloration obtained by means of these oxidation dyes must moreover satisfy a certain number of requirements. Thus it must not have any toxicological disadvantages, it must be able to give shades of the desired intensity and it must be able to withstand external agents (light, bad weather, washing, permanent-waving, perspiration, rubbing).

The dyes must also be able to cover white hair and, lastly, they must be as unselective as possible, i.e. they must give the smallest possible colour differences along the same length of keratin fibre, which may in fact be differently sensitized (i.e. damaged) between its end and its root.

Compositions for the oxidation dyeing of keratin fibres, containing pyrazole derivatives such as 4,5-diaminopyrazoles, 3,4-diaminopyrazoles or 3,4,5-triaminopyrazoles as oxidation base have already been proposed, especially in German patent applications DE 3 843 892, DE 4 234 887, DE 4 234 886, DE 4 234 885 or DE 195 43 988. However, such compositions are not entirely satisfactory since, during the dyeing processes, side reactions take place that can have adverse effects in terms of the harmlessness and of the dyeing properties obtained, and especially the strength and resistance of the colorations with respect to the various attacking factors to which the hair may be subjected.

The invention is aimed at developing novel dye compositions that do not have the drawbacks of the dyes of the prior art, in particular strong dyes that are particularly resistant to the various attacking factors to which the hair may be subjected, and which show good harmlessness.

To this end, one subject of the invention is a composition for the oxidation dyeing of human keratin fibres, and in particular of human keratin fibres such as the hair, comprising, in a medium that is suitable for dyeing:

at least one oxidation base chosen from 4,5- or 3,4-diaminopyrazoles and triaminopyrazoles,
at least one carbonyl compound selected from the compounds of formulae (I), (II) and (III) and the polyimides

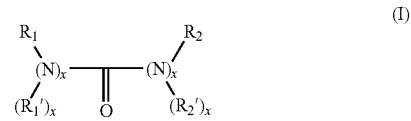

in which
$R_1$, $R_1'$, $R_2$ and $R_2'$ denote, independently of each other, a hydrogen atom; a saturated or unsaturated aliphatic hydrocarbon-based chain containing from 1 to 30 carbon atoms, which may be interrupted with one or more hetero atoms or with one or more carbonyl groups, which is unsubstituted or substituted with one or more groups chosen from hydroxyl, $C_1$-$C_4$ alkoxy, amino, carboxyl, $C_1$-$C_{10}$ alkoxycarbonyl, halogen, nitro, mono- or di($C_1$-$C_4$)alkylamino, mono- or dihydroxy($C_1$-$C_4$)alkylamino or $C_6$-$C_{20}$ aryl groups; a $C_6$-$C_{20}$ aryl group, which is unsubstituted or substituted with one or more groups chosen from hydroxyl, amino, nitro, halogen, carboxyl, ($C_1$-$C_{10}$)alkoxycarbonyl, $C_1$-$C_4$ alkyl, mono- or polyhydroxy($C_1$-$C_4$)alkyl, $C_1$-$C_4$ alkoxy, mono- or di($C_1$-$C_4$)alkylamino or mono- or dihydroxy($C_1$-$C_4$) alkylamino groups,
x denotes 0 or 1, and, when x is equal to 0, $R_1$ and $R_2$ can form, together with the C=O group, a saturated ring optionally fused to one or more benzene nuclei that may be substituted with one or more $C_1$-$C_{10}$ alkyl, $C_1$-$C_{10}$ alkoxy, carboxyl or $C_1$-$C_{10}$ alkoxycarbonyl radicals,

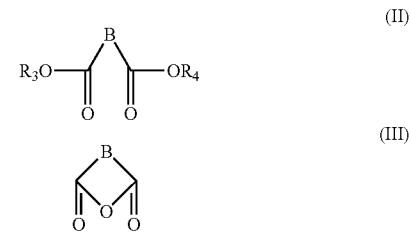

in which:
B denotes a saturated or unsaturated aliphatic hydrocarbon-based chain containing from 1 to 30 carbon atoms, which may be interrupted with one or more hetero atoms or with one or more carbonyl groups, which is unsubstituted or substituted with one or more groups chosen from hydroxyl, $C_1$-$C_4$ alkoxy, amino, carboxyl, $C_1$-$C_{10}$ alkoxycarbonyl, halogen, nitro, mono- or di($C_1$-$C_4$) alkylamino, mono- or dihydroxy($C_1$-$C_4$)alkyl-amino or $C_6$-$C_{20}$ aryl groups; a $C_6$-$C_{20}$ aryl group, which is unsubstituted or substituted with one or more groups chosen from hydroxyl, amino, nitro, halogen, carboxyl, ($C_1$-$C_{10}$)alkoxy-carbonyl, $C_1$-$C_4$ alkyl, mono- or polyhydroxy($C_1$-$C_4$)alkyl, $C_1$-$C_4$ alkoxy, mono- or di($C_1$-$C_4$) alkyl-amino or mono- or dihydroxy($C_1$-$C_4$)alkylamino groups,
$R_3$ and $R_4$, which may be identical or different, represent a hydrogen atom, a $C_1$-$C_{10}$ alkyl, $C_1$-$C_{10}$ monohydroxyalkyl or $C_2$-$C_{10}$ polyhydroxyalkyl radical, Na, K or $NH_4$.

The oxidation dye composition of the invention makes it possible to obtain, with good harmlessness, strong, relatively unselective colorations in varied shades, which show excellent resistance properties both with respect to atmospheric agents such as light and bad weather and with respect to perspiration and various treatments to which the hair may be subjected (shampooing or permanent reshaping).

Except where otherwise mentioned, all the radicals, substituents, groups and chains in the context of the invention are linear or branched, and substituted or unsubstituted.

Among the compounds of formula (I) above that may be mentioned are urea, aliphatic aldehydes or ketones, for instance acetone, aromatic aldehydes or ketones, for instance p-dimethylaminobenzaldehyde or 5-nitrosalicylaldehyde, β-dicarbonyl compounds, for instance α,α-dimethylacetylacetone, γ-pyrones such as 2,6-dimethylpyrone, 2,6-di(ethoxycarbonyl)pyrone and 2-hydroxy-6-methylpyrone, chromones, for instance 2-methylchromone, aldoses or ketoses such as glyceraldehyde, dihydroxyacetone, D-glucose, D-fructose, D-erythrose, D-ribose, D-xylose, D-threose, D-erythrulose and D-sorbose.

Among the compounds of formula (II) above that may be mentioned is maleic acid.

Among the compounds of formula (III) above that may be mentioned is maleic anhydride.

The polyimides are polycondensates derived from tetraacids (or from dianhydrides) and from diamines. Preferably, among these, aromatic polyimides are used. An example that may be mentioned is the polyimides obtained from pyromellitic dianhydride or benzophenone dianhydride. Mention may be made most particularly of the products derived from pyromellitic dianhydride and from 4,4'-diaminodiphenyl ether (Kapton H from the company DuPont).

Among the carbonyl compounds of the invention that are preferably used are urea, aliphatic or aromatic ketones, maleic acid, ketoses or aldoses.

The carbonyl compound(s) in accordance with the invention preferably represent(s) from 0.00001% to 10% by weight and even more preferably from 0.001% to 5% by weight approximately relative to the total weight of the dye composition, and even more preferentially from 0.001% to 3% by weight approximately relative to this weight.

Among the 4,5- or 3,4-diaminopyrazoles that are useful in the dye compositions of the invention, mention may be made particularly of the diamino-pyrazoles chosen from the 4,5- or 3,4-diaminopyrazoles of formula (IV) or (V) below, and/or the addition salts thereof with an acid:

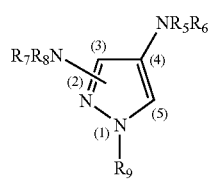

(IV)

in which:

$R_5$, $R_6$, $R_7$, $R_8$ and $R_9$, which may be identical or different, represent a hydrogen atom; a $C_1$-$C_6$ alkyl radical which is unsubstituted or substituted with at least one substituent chosen from OR, NHR, NRR', SR, SOR, $SO_2R$, COR, COOH, $CONH_2$, CONHR, CONRR', $PO(OH)_2$, SH and $SO_3X$, a non-cationic heterocycle, Cl, Br or I, X denoting a hydrogen atom, Na, K or $NH_4$, and R and R', which may be identical or different, representing a $C_1$-$C_4$ alkyl or alkenyl; a $C_2$-$C_4$ hydroxyalkyl radical; a $C_2$-$C_4$ aminoalkyl radical; a phenyl radical; a phenyl radical substituted with a halogen atom or a $C_1$-$C_4$ alkyl, $C_1$-$C_4$ alkoxy, nitro, trifluoromethyl, amino or $C_1$-$C_4$ alkylamino radical; a benzyl radical; a benzyl radical substituted with a halogen atom or with a $C_1$-$C_4$ alkyl, $C_1$-$C_4$ alkoxy, methylenedioxy or amino radical; a radical

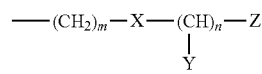

in which m and n are integers, which may be identical or different, between 0 and 3 inclusive, X represents an oxygen atom or an NH group, Y represents a hydrogen atom or a $C_1$-$C_4$ alkyl radical, and Z represents a methyl radical when n is equal to 0, or Z represents a $C_1$-$C_4$ alkyl radical, a group OR or NR"R'" when n is greater than or equal to 1, R" and R"', which may be identical or different, denoting a hydrogen atom or a $C_1$-$C_4$ alkyl radical; or $R_9$ forms with the nitrogen atom of the group $NR_7R_8$ in position 5 an at least 4-membered heterocycle, $R_{10}$ represents a $C_1$-$C_6$ alkyl radical; a $C_1$-$C_4$ hydroxy-alkyl radical; a $C_1$-$C_4$ aminoalkyl radical; a ($C_1$-$C_4$)-alkylamino($C_1$-$C_4$)alkyl radical; a di ($C_1$-$C_4$)alkylamino-($C_1$-$C_4$)alkyl radical; a hydroxy($C_1$-$C_4$)alkylamino($C_1$-$C_4$)-alkyl radical; a ($C_1$-$C_4$)alkoxymethyl radical; a phenyl radical; a phenyl radical substituted with a halogen atom or with a $C_1$-$C_4$ alkyl, $C_1$-$C_4$ alkoxy, nitro, trifluoromethyl, amino or $C_1$-$C_4$ alkylamino radical; a benzyl radical; a benzyl radical substituted with a halogen atom or with a $C_1$-$C_4$ alkyl, $C_1$-$C_4$ alkoxy, nitro, trifluoromethyl, amino or $C_1$-$C_4$ alkylamino radical; a heterocycle chosen from thiophene, furan and pyridine, or a radical —$(CH_2)_p$—O—$(CH_2)_q$—OR", in which p and q are integers, which may be identical or different, between 1 and 3 inclusive and R" is as defined above, it being understood that:

at least one of the radicals $R_5$, $R_6$, $R_7$ and $R_8$ represents a hydrogen atom.

Among the triaminopyrazoles that are useful as oxidation bases in the dye compositions in accordance with the invention, mention may be made more particularly of the compounds of formula (VI) below, and the addition salts thereof with an acid:

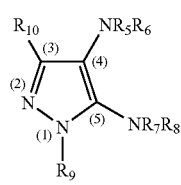

(V)

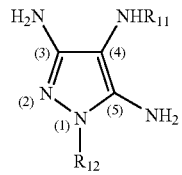

(VI)

in which:

R₁₁ and R₁₂, which may be identical or different, represent a hydrogen atom or a $C_1$-$C_4$ alkyl or $C_2$-$C_4$ hydroxyalkyl radical.

Among the 4,5- or 3,4-diaminopyrazoles of formula (IV) above that may be mentioned more particularly are 4,5-diamino-1-(4'-methoxybenzyl)-pyrazole, 4,5-diamino-1-(4'-methylbenzyl)pyrazole, 4,5-diamino-1-(4'-chlorobenzyl)pyrazole, 4,5-diamino-1-(3'-methoxybenzyl)pyrazole, 4-amino-1-(4'-methoxy-benzyl)-5-methylaminopyrazole, 4-amino-5-(β-hydroxy-ethyl)amino-1-(4'-methoxybenzyl)pyrazole, 4-amino-5-(β-hydroxyethyl)amino-1-methylpyrazole, 4-amino-(3)-5-methylaminopyrazole, 3-(5), 4-diaminopyrazole, 4,5-diamino-1-methylpyrazole, 4,5-diamino-1-ethyl-pyrazole, 4,5-diamino-1-isopropylpyrazole, 4,5-diamino-1-hydroxyethylpyrazole, 4,5-diamino-1-benzylpyrazole, 4-diamino-5-hydroxyethylamino-1-hydroxyethylpyrazole, 4-diamino-5-methylamino-1-hydroxyethylpyrazole, 3-amino-4,5,7,8-tetrahydropyrazolo[1,5-a]pyrimidine, 7-amino-2,3-dihydro-1H-imidazole[1,2-b]pyrazole, 3-amino-8-methyl-4,5,7,8-tetrahydropyrazolo[1,5-a]-pyrimidine, 2-(4,5-diamino-1-pyrazolyl)-1-ethanesulphonic acid, 2-(4,5-diamino-1-pyrazolyl)acetamide, 2-(4,5-diamino-1-pyrazolyl)acetic acid, 2-(2-dimethylaminoethyl)-2H-pyrazole-3,4-diamine and 2-(2-methoxyethyl)-2H-pyrazole-3,4-diamine, and the addition salts thereof with an acid.

The diaminopyrazoles that are useful in the present invention may be obtained via synthetic processes that are well known to those skilled in the art. For example, the 4,5-diaminopyrazoles of formula (V) may be prepared according to the synthetic process as described, for example, in French patent application FR-A-2 733 749.

Among the 4,5-diaminopyrazoles of formula (V) above that may be mentioned more particularly are:
1-benzyl-4,5-diamino-3-methylpyrazole,
4,5-diamino-1-(β-hydroxyethyl)-3-(4'-methoxyphenyl)-pyrazole,
4,5-diamino-1-(β-hydroxyethyl)-3-(4'-methylphenyl)-pyrazole,
4,5-diamino-1-(β-hydroxyethyl)-3-(3'-methylphenyl)-pyrazole,
4,5-diamino-3-methyl-1-isopropylpyrazole,
4,5-diamino-3-(4'-methoxyphenyl)-1-isopropylpyrazole,
4,5-diamino-1-ethyl-3-methylpyrazole,
4,5-diamino-1-ethyl-3-(4'-methoxyphenyl)pyrazole,
4,5-diamino-1-hydroxymethyl-1-methylpyrazole,
4,5-diamino-1-ethyl-3-hydroxymethylpyrazole,
4,5-diamino-3-hydroxymethyl-1-isopropylpyrazole,
4,5-diamino-3-hydroxymethyl-1-tert-butylpyrazole,
4,5-diamino-3-hydroxymethyl-1-phenylpyrazole,
4,5-diamino-3-hydroxymethyl-1-(2'-methoxyphenyl)-pyrazole,
4,5-diamino-3-hydroxymethyl-1-(3'-methoxyphenyl)-pyrazole,
4,5-diamino-3-hydroxymethyl-1-(4'-methoxyphenyl)-pyrazole,
1-benzyl-4,5-diamino-3-hydroxymethylpyrazole,
4,5-diamino-3-methyl-1-(2'-methoxyphenyl)pyrazole,
4,5-diamino-3-methyl-1-(3'-methoxyphenyl)pyrazole,
4,5-diamino-3-methyl-1-(4'-methoxyphenyl)pyrazole,
3-aminomethyl-4,5-diamino-1-methylpyrazole,
3-aminomethyl-4,5-diamino-1-ethylpyrazole,
3-aminomethyl-4,5-diamino-1-isopropylpyrazole,
3-aminomethyl-4,5-diamino-1-tert-butylpyrazole,
4,5-diamino-3-dimethylaminomethyl-1-methylpyrazole,
4,5-diamino-3-dimethylaminomethyl-1-ethylpyrazole,
4,5-diamino-3-dimethylaminomethyl-1-isopropyl-pyrazole,
4,5-diamino-3-dimethylaminomethyl-1-tert-butyl-pyrazole,
4,5-diamino-3-ethylaminomethyl-1-methylpyrazole,
4,5-diamino-3-ethylaminomethyl-1-ethylpyrazole,
4,5-diamino-3-ethylaminomethyl-1-isopropylpyrazole,
4,5-diamino-3-ethylaminomethyl-1-tert-butylpyrazole,
4,5-diamino-3-methylaminomethyl-1-methylpyrazole,
4,5-diamino-3-methylaminomethyl-1-isopropylpyrazole,
4,5-diamino-1-ethyl-3-methylaminomethylpyrazole,
1-tert-butyl-4,5-diamino-3-methylaminomethylpyrazole,
4,5-diamino-3-[(β-hydroxyethyl)aminomethyl]-1-methyl-pyrazole,
4,5-diamino-3-[(β-hydroxyethyl)aminomethyl]-1-iso-propylpyrazole,
4,5-diamino-1-ethyl-3-[(β-hydroxyethyl)aminomethyl]-pyrazole,
1-tert-butyl-4,5-diamino-3-[(β-hydroxyethyl)amino-methyl]pyrazole,
4-amino-5-(β-hydroxyethyl)amino-1,3-dimethylpyrazole,
4-amino-5-(β-hydroxyethyl)amino-1-isopropyl-3-methyl-pyrazole,
4-amino-5-(β-hydroxyethyl)amino-1-ethyl-3-methyl-pyrazole,
4-amino-5-(β-hydroxyethyl)amino-1-tert-butyl-3-methylpyrazole,
4-amino-5-(β-hydroxyethyl)amino-1-phenyl-3-methyl-pyrazole,
4-amino-5-(β-hydroxyethyl)amino-1-(2-methoxyphenyl)-3-methylpyrazole,
4-amino-5-(β-hydroxyethyl)amino-1-(3-methoxyphenyl)-3-methylpyrazole,
4-amino-5-(β-hydroxyethyl)amino-1-(4-methoxyphenyl)-3-methylpyrazole,
4-amino-5-(β-hydroxyethyl)amino-1-benzyl-3-methyl-pyrazole,
4-amino-1-ethyl-3-methyl-5-methylaminopyrazole,
4-amino-1-tert-butyl-3-methyl-5-methylaminopyrazole,
4,5-diamino-1,3-dimethylpyrazole,
4,5-diamino-3-tert-butyl-1-methylpyrazole,
4,5-diamino-1-tert-butyl-3-methylpyrazole,
4,5-diamino-1-methyl-3-phenylpyrazole,
4,5-diamino-1-(β-hydroxyethyl)-3-methylpyrazole,
4,5-diamino-1-(β-hydroxyethyl)-3-phenylpyrazole,
4,5-diamino-1-methyl-3-(2'-chlorophenyl)pyrazole,
4,5-diamino-1-methyl-3-(4'-chlorophenyl)pyrazole,
4,5-diamino-1-methyl-3-(3'-trifluoromethylphenyl)-pyrazole,
4,5-diamino-1,3-diphenylpyrazole,
4,5-diamino-3-methyl-1-phenylpyrazole,
4-amino-1,3-dimethyl-5-phenylaminopyrazole,
4-amino-1-ethyl-3-methyl-5-phenylaminopyrazole,
4-amino-1,3-dimethyl-5-methylaminopyrazole,
4-amino-3-methyl-1-isopropyl-5-methylaminopyrazole,
4-amino-3-isobutoxymethyl-1-methyl-5-methylamino-pyrazole,
4-amino-3-methoxyethoxymethyl-1-methyl-5-methylamino-pyrazole,
4-amino-3-hydroxymethyl-1-methyl-5-methylamino-pyrazole,
4-amino-1,3-diphenyl-5-phenylaminopyrazole,
4-amino-3-methyl-5-methylamino-1-phenylpyrazole,
4-amino-1,3-dimethyl-5-hydrazinopyrazole,
5-amino-3-methyl-4-methylamino-1-phenylpyrazole,
5-amino-1-methyl-4-(N,N-methylphenyl)amino-3-(4'-chlorophenyl) pyrazole,
5-amino-3-ethyl-1-methyl-4-(N,N-methylphenyl)amino-pyrazole, 5-amino-1-methyl-4-(N,N-methylphenyl)amino-3-phenyl-pyrazole,
5-amino-3-ethyl-4-(N,N-methylphenyl)aminopyrazole,
5-amino-4-(N,N-methylphenyl)amino-3-phenylpyrazole,
5-amino-4-(N,N-methylphenyl)amino-3-(4'-methylphenyl)-pyrazole,
5-amino-3-(4'-chlorophenyl)-4-(N,N-methylphenyl)-aminopyrazole,
5-amino-3-(4'-methoxyphenyl)-4-(N,N-methylphenyl)-aminopyrazole,
4-amino-5-methylamino-3-phenylpyrazole,
4-amino-5-ethylamino-3-phenylpyrazole,
4-amino-5-ethylamino-3-(4'-methylphenyl)pyrazole,
4-amino-3-phenyl-5-propylaminopyrazole,
4-amino-5-butylamino-3-phenylpyrazole,
4-amino-3-phenyl-5-phenylaminopyrazole,
4-amino-5-benzylamino-3-phenylpyrazole,
4-amino-5-(4'-chlorophenyl)amino-3-phenylpyrazole,
4-amino-3-(4'-chlorophenyl)-5-phenylaminopyrazole,
4-amino-3-(4'-methoxyphenyl)-5-phenylaminopyrazole,
1-(4'-chlorobenzyl)-4,5-diamino-3-methylpyrazole,
4,5-diamino-3-hydroxymethyl-1-isopropylpyrazole,
4-amino-1-ethyl-3-methyl-5-methylaminopyrazole,
4-amino-5-(2'-aminoethyl)amino-1,3-dimethylpyrazole, and the addition salts thereof with an acid.

Among the 4,5- or 3,4-diaminopyrazoles of formula (IV) above, the following are more particularly preferred:
4,5-diamino-1-benzylpyrazole,
4,5-diamino-1-(4'-chlorobenzyl)pyrazole,
4,5-diamino-1-methylpyrazole,
4,5-diamino-1-hydroxyethylpyrazole,
2-(2-methoxyethyl)-2H-pyrazole-3,4-diamine and the addition salts thereof with an acid.

Among the 4,5-diaminopyrazoles of formula (V) above, the following are more particularly preferred:
4,5-diamino-1,3-dimethylpyrazole,
4,5-diamino-3-methyl-1-phenylpyrazole,
4,5-diamino-1-methyl-3-phenylpyrazole,
4-amino-1,3-dimethyl-5-hydrazinopyrazole,
1-benzyl-4,5-diamino-3-methylpyrazole,
4,5-diamino-3-tert-butyl-1-methylpyrazole,
4,5-diamino-1-tert-butyl-3-methylpyrazole,
4,5-diamino-1-(β-hydroxyethyl)-3-methylpyrazole,
4,5-diamino-1-ethyl-3-methylpyrazole,
4,5-diamino-1-ethyl-3-(4'-methoxyphenyl)pyrazole,
4,5-diamino-1-ethyl-3-hydroxymethylpyrazole,
4,5-diamino-3-hydroxymethyl-1-methylpyrazole,
4,5-diamino-3-hydroxymethyl-1-isopropylpyrazole,
4,5-diamino-3-methyl-1-isopropylpyrazole,
4-amino-5-(2'-aminoethyl)amino-1,3-dimethylpyrazole, and the addition salts thereof with an acid.

Among the triaminopyrazoles of formula (VI) above that may be mentioned more particularly are 3,4,5-triaminopyrazole, 1-methyl-3,4,5-triamino-pyrazole, 3,5-diamino-1-methyl-4-methylaminopyrazole and 3,5-diamino-4-(β-hydroxyethyl)amino-1-methyl-pyrazole, and the additions salts thereof with an acid.

The 4,5- or 3,4-diaminopyrazole(s) and/or the triaminopyrazole(s) in accordance with the invention and/or the corresponding addition salt(s) with an acid preferably represent from 0.0005% to 12% by weight approximately relative to the total weight of the dye composition and more preferably from 0.005% to 6% by weight approximately relative to this weight.

Preferably, the weight ratio of the carbonyl compound(s) to the 4,5- or 3,4-diaminopyrazole(s) and/or the triaminopyrazole(s) and/or the addition salt(s) with an acid is between 0.001 and 100 and even more preferably between 0.01 and 10.

The dye compositions in accordance with the invention preferably contain at least one coupler. The couplers that may be used are those conventionally used for oxidation dyeing, and especially meta-phenylene-diamines, meta-aminophenols, meta-diphenols, naphthol derivatives and heterocyclic couplers.

The meta-phenylenediamines, meta-aminophenols and meta-diphenols which may be used as additional couplers in the dye composition in accordance with the invention are preferably chosen from the compounds corresponding to formula (1) below, and the addition salts thereof with an acid:

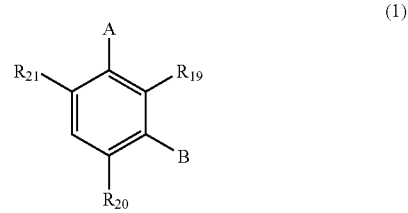

(1)

in which:
A and B, which may be identical or different, represent a hydroxyl, amino or —NHR$_{22}$ radical in which R$_{22}$ represents a C$_1$-C$_4$ alkyl, C$_1$-C$_4$ monohydroxy-alkyl or C$_2$-C$_4$ polyhydroxyalkyl radical,
R$_{19}$, R$_{20}$ and R$_{21}$, which may be identical or different, represent a hydrogen atom or a halogen atom such as a bromine, chlorine, iodine or fluorine atom, or a C$_1$-C$_4$ alkyl, C$_1$-C$_4$ alkoxy, C$_1$-C$_4$ monohydroxyalkyl, C$_2$-C$_4$ polyhydroxyalkyl, C$_1$-C$_4$ monohydroxyalkoxy or C$_2$-C$_4$ polyhydroxyalkoxy radical.

Among the compounds of formula (1) above, mention may be made in particular of 2-methyl-5-aminophenol, 2-methyl-5-amino-6-chlorophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethyl-amino)-1-methoxybenzene, 1,3-diaminobenzene and 2,6-bis(β-hydroxyethylamino)toluene, and the addition salts thereof with an acid.

The heterocyclic coupler(s) which may be used as additional couplers in the dye composition in accordance with the invention can be chosen in particular from indole derivatives, indoline derivatives, pyridine derivatives, pyrimidine derivatives and pyrazolones, and the addition salts thereof with an acid.

Among these heterocyclic couplers, mention may be made in particular, for example, of sesamol, 1-N-(β-hydroxyethyl)amino-3',4-methylenedioxybenzene, 6-hydroxyindole, 4-hydroxyindole, 4-hydroxy-N-methyl-indole, 6-hydroxyindoline, 6-hydroxybenzomorpholine, 2,6-dihydroxy-4-methylpyridine, 3,5-diamino-2,6-di-methoxypyridine, 2-amino-3-hydroxypyridine, 1-H-3-methylpyrazol-5-one and 1-phenyl-3-methylpyrazol-5-one, and the addition salts thereof with an acid.

Among the naphthol derivatives that may be mentioned are α-naphthol and 2-methyl-1-naphthol.

The additional coupler(s) preferably represent(s) from 0.0001% to 10% by weight approximately relative to the total weight of the dye composition, and even more preferably from 0.005% to 5% by weight approximately relative to this weight.

The dye compositions in accordance with the invention may also contain other oxidation bases conventionally used for oxidation dyeing, other than a diaminopyrazole and a triaminopyrazole and/or direct dyes, especially to modify the shades or to enrich them with glints.

The additional oxidation bases that may be used in the context of the present invention are chosen from those conventionally known in oxidation dyeing, and among which mention may be made especially of ortho- and para-phenylenediamines, double bases, ortho- and para-aminophenols, and heterocyclic bases other than the pyrazoles of the invention, and also the addition salts thereof with an acid, and especially:
(I) the para-phenylenediamines of formula (2) below, and the addition salts thereof with an acid:

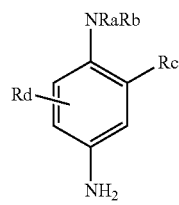

(2)

in which:
$R_a$ represents a hydrogen atom, a $C_1$-$C_4$ alkyl radical, a $C_1$-$C_4$ monohydroxyalkyl radical, a $C_2$-$C_4$ polyhydroxy-alkyl radical, a ($C_1$-$C_4$)alkoxy($C_1$-$C_4$)alkyl radical, a $C_1$-$C_4$ alkyl radical substituted with a nitrogenous group, a phenyl radical or a 4'-aminophenyl radical;
$R_b$ represents a hydrogen atom, a $C_1$-$C_4$ alkyl radical, a $C_1$-$C_4$ monohydroxyalkyl radical, a $C_2$-$C_4$ polyhydroxy-alkyl radical, a ($C_1$-$C_4$)alkoxy($C_1$-$C_4$)alkyl radical or a $C_1$-$C_4$ alkyl radical substituted with a nitrogenous group;
$R_c$ represents a hydrogen atom, a halogen atom such as a chlorine atom, a $C_1$-$C_4$ alkyl radical, a sulfo radical, a carboxyl radical, a $C_1$-$C_4$ monohydroxyalkyl radical, a $C_1$-$C_4$ hydroxyalkoxy radical, an acetylamino($C_1$-$C_4$)-alkoxy radical, a $C_1$-$C_4$ mesylaminoalkoxy radical or a carbamoylamino ($C_1$-$C_4$) alkoxy radical,
$R_d$ represents a hydrogen or halogen atom or a $C_1$-$C_4$ alkyl radical,
$R_a$ and $R_b$ may also form with the nitrogen atom that bears them a 5- or 6-membered nitrogenous heterocycle optionally substituted with one or more alkyl, hydroxyl or ureido groups.

Among the nitrogenous groups of formula (2) above, mention may be made in particular of amino, mono($C_1$-$C_4$)alkylamino, di($C_1$-$C_4$)alkylamino, tri($C_1$-$C_4$)-alkylamino, monohydroxy($C_1$-$C_4$)alkylamino, imidazolinium and ammonium radicals.

Among the para-phenylenediamines of formula (2) above, mention may be made more particularly of para-phenylenediamine, para-tolylenediamine, 2-chloro-para-phenylenediamine, 2,3-dimethyl-para-phenylene-diamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-3-methylaniline, 4-amino-3-chloro-N,N-bis(β-hydroxyethyl)aniline, 2-p-hydroxy-ethyl-para-phenylenediamine, 2-fluoro-para-phenylene-diamine, 2-isopropyl-para-phenylenediamine, N-(β-hydroxypropyl)-para-phenylenediamine, 2-hydroxy-methyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylene-diamine, N-phenyl-para-phenylenediamine and 2-β-hydroxyethyloxy-para-phenylenediamine, and the addition salts thereof with an acid.

Among the para-phenylenediamines of formula (2) above, para-phenylenediamine, para-tolylenediamine, 2-isopropyl-para-phenylenediamine, 2-β-hydroxyethyl-para-phenylenediamine, 2-p-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine and 2-chloro-para-phenylenediamine, and the addition salts thereof with an acid are most particularly preferred.

(II) the double bases are compounds comprising at least two aromatic nuclei bearing amino and/or hydroxyl groups.

Among the double bases which can be used as oxidation bases in the dye compositions in accordance with the invention, mention may be made in particular of the compounds corresponding to formula (3) below, and the addition salts thereof with an acid:

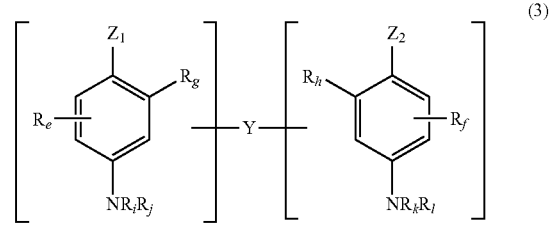

(3)

in which:
$Z_1$ and $Z_2$, which may be identical or different, represent a hydroxyl or —$NH_2$ radical which may be substituted with a $C_1$-$C_4$ alkyl radical or with a linker arm Y;
the linker arm Y represents a linear or branched alkylene chain containing from 1 to 14 carbon atoms, which may be interrupted by or terminated with one or more nitrogenous groups and/or one or more hetero atoms such as oxygen, sulphur or nitrogen atoms, and optionally substituted with one or more hydroxyl or $C_1$-$C_6$ alkoxy radicals;
$R_e$ and $R_f$ represent a hydrogen or halogen atom, a $C_1$-$C_4$ alkyl radical, a $C_1$-$C_4$ monohydroxyalkyl radical, a $C_2$-$C_4$ polyhydroxyalkyl radical, a $C_1$-$C_4$ aminoalkyl radical or a linker arm Y;
$R_g$, $R_h$, $R_i$, $R_j$, $R_k$ and $R_l$, which may be identical or different, represent a hydrogen atom, a linker arm Y or a $C_1$-$C_4$ alkyl radical;
it being understood that the compounds of formula (3) contain only one linker arm Y per molecule.

Among the nitrogenous groups of formula (3) above, mention may be made in particular of amino, mono($C_1$-$C_4$)alkylamino, di($C_1$-$C_4$)alkylamino, tri($C_1$-$C_4$)-alkylamino, monohydroxy($C_1$-$C_4$)alkylamino, imidazolinium and ammonium radicals.

Among the double bases of formula (3) above, mention may be made more particularly of N,N'-bis(β-hydroxyethyl)-

N,N'-bis(4'-aminophenyl)-1,3-diamino-propanol, N,N'-bis(β-hydroxyethyl)-N,N'-bis(4'-amino-phenyl)ethylenediamine, N,N'-bis(4-aminophenyl)-tetramethylenediamine, N,N'-bis(β-hydroxyethyl)-N,N'-bis(4-aminophenyl)tetramethylenediamine, N,N'-bis-(4-methylaminophenyl)tetramethylenediamine, N,N'-bis-(ethyl)-N,N'-bis(4'-amino-3'-methylphenyl)ethylene-diamine and 1,8-bis(2,5-diaminophenoxy)-3,6-dioxa-octane, and the addition salts thereof with an acid. Among these double bases of formula (3), N,N'-bis(β-hydroxyethyl)-N,N'-bis(4'-aminophenyl)-1,3-diamino-propanol and 1,8-bis(2,5-diaminophenoxy)-3,6-dioxa-octane, or one of the addition salts thereof with an acid, are particularly preferred.

(III) the para-aminophenols corresponding to formula (4) below, and the addition salts thereof with an acid:

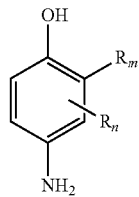

(4)

in which:
$R_a$ represents a hydrogen or halogen atom such as fluorine or a $C_1$-$C_4$ alkyl, $C_1$-$C_4$ monohydroxyalkyl, ($C_1$-$C_4$)alkoxy($C_1$-$C_4$)alkyl, $C_1$-$C_4$ aminoalkyl or hydroxy($C_1$-$C_4$)alkylamino ($C_1$-$C_4$)alkyl radical,
$R_n$ represents a hydrogen or halogen atom such as fluorine or a $C_1$-$C_4$-alkyl, $C_1$-$C_4$ monohydroxyalkyl, $C_2$-$C_4$ polyhydroxyalkyl, $C_1$-$C_4$ aminoalkyl, $C_1$-$C_4$ cyanoalkyl or ($C_1$-$C_4$) alkoxy($C_1$-$C_4$) alkyl radical.

Among the para-aminophenols of formula (4) above, mention may be made more particularly of para-aminophenol, 4-amino-3-methylphenol, 4-amino-3-fluoro-phenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and the addition salts thereof with an acid.

(IV) the ortho-aminophenols that may be used as oxidation bases in the context of the present invention are chosen especially from 2-aminophenol, 2-amino-1-hydroxy-5-methylbenzene, 2-amino-1-hydroxy-6-methyl-benzene and 5-acetamido-2-aminophenol, and the addition salts thereof with an acid.

(V) among the heterocyclic bases which can be used as oxidation bases in the dye compositions in accordance with the invention, mention may be made more particularly of pyridine derivatives, pyrimidine derivatives and pyrazole derivatives and the addition salts thereof with an acid.

Among the pyridine derivatives, mention may be made more particularly of the compounds described, for example, in patents GB 1,026,978 and GB 1,153,196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Among the pyrimidine derivatives, mention may be made more particularly of the compounds described, for example, in patents DE 2 359 399; JP 88-169 571; JP 91-10659 or patent application WO96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-tri-aminopyrimidine, and pyrazolopyrimidine derivatives such as those mentioned in patent application FR-A-2 750 048, and among which mention may be made of pyrazolo[1,5-a]pyrimidine-3,7-diamine, 2,5-dimethyl-pyrazolo[1,5-a]pyrimidine-3,7-diamine, pyrazolo[1,5-a]-pyrimidine-3,5-diamine, 2,7-dimethylpyrazolo[1,5-a]-pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]-pyrimidin-3-yl)(2-hydroxyethyl)amino]ethanol, 5,6-di-methylpyrazolo[1,5-a]pyrimidine-3,7-diamine, 2,6-dimethylpyrazolo[1,5-a]pyrimidine-3,7-diamine and 2,5,N7,N7-tetramethylpyrazolo[1,5-a]pyrimidine-3,7-diamine, the addition salts thereof, and the tautomeric forms thereof, when a tautomeric equilibrium exists, and the addition salts thereof with an acid.

According to the present invention, the additional oxidation bases may preferably represent from 0.0005% to 12% by weight approximately relative to the total weight of the dye composition.

In general, the addition salts with an acid which can be used in the context of the dye compositions of the invention (oxidation bases and couplers) are chosen in particular from the hydrochlorides, hydrobromides, sulphates, tartrates, lactates and acetates.

The medium that is suitable for the dyeing (or the support) generally consists of water or of a mixture of water and at least one organic solvent in order to dissolve the compounds that would not be sufficiently soluble in water. By way of organic solvent, mention may be made, for example, of $C_1$-$C_4$ lower alkanols such as ethanol and isopropanol; glycerol; glycols and glycol ethers such as 2-butoxyethanol, propylene glycol, propylene glycol monomethyl ether, diethylene glycol monoethyl ether and monomethyl ether, and aromatic alcohols such as benzyl alcohol or phenoxyethanol, similar products and mixtures thereof.

The solvents can be present in proportions preferably of between 1 and 40% by weight approximately relative to the total weight of the dye composition, and even more preferably between 5 and 30% by weight approximately.

The pH of the dye composition in accordance with the invention is generally between 3 and 12 approximately and preferably between 5 and 11 approximately. It may be adjusted to the desired value with the aid of acidifying or basifying agents commonly used in the dyeing of keratin fibres.

Among the acidifying agents, mention may be made, by way of example, of inorganic or organic acids such as hydrochloric acid, orthophosphoric acid, carboxylic acids such as tartaric acid, citric acid or lactic acid, and sulphonic acids.

Among the basifying agents that may be mentioned, for example, are aqueous ammonia, alkaline carbonates, alkanolamines such as monoethanolamine, diethanolamine and triethanolamine and derivatives thereof, sodium hydroxide, potassium hydroxide and the compounds of formula (5) below:

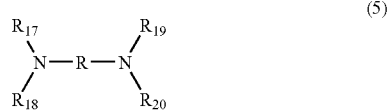

(5)

in which R is a propylene residue optionally substituted with a hydroxyl group or a $C_1$-$C_4$ alkyl radical; $R_{17}$, $R_{18}$, $R_{19}$ and $R_{20}$, which may be identical or different, represent a hydrogen atom or a $C_1$-$C_4$ alkyl or $C_1$-$C_4$ hydroxyalkyl radical.

The dye composition in accordance with the invention can also contain various adjuvants used conventionally in compositions for dyeing the hair, such as anionic, cationic, non-ionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, conditioners, such as, for example, volatile or non-volatile silicones, which are modified or unmodified, film-forming agents, ceramides, preserving agents and opacifiers.

Needless to say, a person skilled in the art will take care to select this or these optional complementary compound(s) such that the advantageous properties intrinsically associated with the combination in accordance with the invention is (are) not, or not substantially, adversely affected by the addition or additions envisaged.

The dye composition in accordance with the invention can be in various forms, such as in the form of liquids, creams or gels or in any other form that is suitable for dyeing keratin fibres, and especially human hair.

A subject of the invention is also a process for dyeing keratin fibres, and in particular human keratin fibres such as the hair, using the dye composition as defined above.

According to this process, the dye composition as defined above is applied to the fibres, the colour being developed at acidic, neutral or alkaline pH using an oxidizing agent, this oxidizing agent possibly being added just at the time of use to the dye composition or by means of an oxidizing composition applied simultaneously or sequentially.

According to one particularly preferred embodiment of the dyeing process according to the invention, the dye composition described above is mixed, at the time of use, with an oxidizing composition containing, in a medium which is suitable for dyeing, at least one oxidizing agent present in an amount which is sufficient to develop a coloration. The mixture obtained is then applied to the keratin fibres and is left to stand on them for about 3 to 60 minutes, preferably about 5 to 40 minutes, after which the fibres are rinsed, washed with shampoo, rinsed again and dried.

The oxidizing agent present in the oxidizing composition as defined above may be chosen from the oxidizing agents conventionally used for the oxidation dyeing of keratin fibres, and among which mention may be made of hydrogen peroxide, urea peroxide, alkali metal bromates, persalts such as perborates, percarbonates and persulphates, and peracids. Hydrogen peroxide is particularly preferred.

The pH of the oxidizing composition containing the oxidizing agent as defined above is such that, after mixing it with the dye composition, the pH of the resulting composition applied to the keratin fibres preferably ranges between about 3 and 12 and even more preferably between 5 and 11. It is adjusted to the desired value by means of acidifying or basifying agents usually used for the dyeing of keratin fibres and as defined above.

The oxidizing composition as defined above can also contain various adjuvants conventionally used in compositions for dyeing the hair and as defined above.

The dye composition that is applied to the keratin fibres can be in various forms, such as in the form of liquids, creams or gels or any other form that is suitable for dyeing keratin fibres, and in particular human hair.

According to one variant, a composition containing at least the carbonyl compound is applied to these fibres in a first stage, and a composition containing at least one diaminopyrazole is applied in a second stage, the application of the composition containing the carbonyl compound(s) possibly being followed by a rinsing step, the colour being developed using an oxidizing agent.

Another subject of the invention is a multi-compartment device or dyeing "kit" or any other multi-compartment packaging system, a first compartment of which contains the dye composition as defined above and a second compartment of which contains the oxidizing composition as defined above. These devices may be equipped with a means for applying the desired mixture to the hair, such as the devices described in patent FR-2 586 913 in the name of the Applicant.

According to a different embodiment, the device comprises at least three compartments, a first compartment that contains the carbonyl compound that is useful for the invention, a second compartment that contains a diaminopyrazole, and a third compartment that contains an oxidizing composition.

The examples that follow are intended to illustrate the invention without, however, limiting its scope.

EXAMPLES

Dyeing Examples 1 to 10

The dye compositions below, in accordance with the invention, were prepared (contents in grams): AM denotes Active Material

|  | EXAMPLES | | | | | | | | | |
|---|---|---|---|---|---|---|---|---|---|---|
|  | 1 | 2 | 3 | 4 | 5 | 6 | 7 | 8 | 9 | 10 |
| 4,5-Diamino-1-β-hydroxyethyl-pyrazole dihydrochloride (oxidation base) | 0.645 | 0.645 | 0.645 | 0.645 | 0.645 | 0.645 | 0.645 | 0.645 | 0.645 | 0.645 |
| 3-Amino-6-methyl-phenol (coupler) | 0.369 | 0.369 | 0.369 | 0.369 | 0.369 | 0.369 | 0.369 | 0.369 | 0.369 | 0.369 |

-continued

| | EXAMPLES | | | | | | | | | |
|---|---|---|---|---|---|---|---|---|---|---|
| | 1 | 2 | 3 | 4 | 5 | 6 | 7 | 8 | 9 | 10 |
| Urea (carbonyl compound according to the invention) | 0.1 | — | — | — | — | — | — | — | — | — |
| p-Dimethylamino-benzaldehyde (carbonyl compound according to the invention) | — | 0.05 | — | — | — | — | — | — | — | — |
| 2-Hydroxy-6-methylpyrone (carbonyl compound according to the invention) | — | — | 0.15 | — | — | — | — | — | — | — |
| 2-Methylchromone (carbonyl compound according to the invention) | — | — | — | 0.2 | — | — | — | — | — | — |
| D-Fructose | — | — | — | — | 0.5 | — | — | — | — | — |
| Maleic acid (carbonyl compound according to the invention) | — | — | — | — | — | 0.5 | — | — | — | — |
| Maleic anhydride (carbonyl compound according to the invention) | — | — | — | — | — | — | 0.4 | — | — | — |
| Kapton H (DuPont) | — | — | — | — | — | — | — | 1 AM | — | — |
| Acetone (carbonyl compound according to the invention) | — | — | — | — | — | — | — | — | 0.1 | — |
| α,α-Dimethyl-acetylacetone (carbonyl compound according to the invention) | — | — | — | — | — | — | — | — | — | 0.2 |
| Common dye support | () | () | () | () | () | () | () | () | () | () |
| Demineralized water qs | 100 g | 100 g | 100 g | 100 g | 100 g | 100 g | 100 g | 100 g | 100 g | 100 g |

(**) common dye support containing:
Oleyl alcohol polyglycerolated with 2 mol of glycerol 4.0 g
Oleyl alcohol polyglycerolated with 4 mol of glycerol, containing 78% active material (AM) 5.69 g AM
Oleic acid 3.0 g
Oleylamine containing 2 mol of ethylene oxide, sold under the trade name Ethomeen 012 by the company Akzo 7.0 g
Diethylaminopropyl laurylaminosuccinamate, sodium salt, containing 55% AM 3.0 g AM
Oleyl alcohol 5.0 g
Oleic acid diethanolamide 12.0 g
Propylene glycol 3.5 g
Ethyl alcohol 7.0 g
Dipropylene glycol 0.5 g
Propylene glycol monomethyl ether 9.0 g
Sodium metabisulphite as an aqueous solution containing 35% A M 0.455 g A M
Ammonium acetate 0.8 g
Antioxidant, sequestering agent qs
Fragrance, preserving agent qs
Aqueous ammonia containing 20% $NH_3$ 10 g At the time of use, each dye composition above was mixed with an equal amount by weight of an oxidizing composition consisting of a 20-volumes aqueous hydrogen peroxide solution (6% by weight).

Each resulting composition was applied for 30 minutes to locks of natural grey hair containing 90% white hairs. The locks of hair were then rinsed, washed with a standard shampoo and then dried.

In all cases, a strong and resistant red shade, with good harmlessness, is obtained.

Dyeing Examples 11 to 13

The dye compositions below, in accordance with the invention, were prepared (amounts in grams):

| | EXAMPLE | | |
|---|---|---|---|
| | 11 | 12 | 13 |
| 4,5-Diamino-1-ethyl-3-methyl-pyrazole dihydrochloride (oxidation base) | 0.639 | 0.639 | — |
| 3,4,5-Triaminopyrazole dihydrochloride (oxidation base) | — | — | 0.667 |
| 3-Amino-6-methylphenol (coupler) | 0.369 | 0.369 | 0.369 |
| Urea (carbonyl compound according to the invention) | 0.1 | — | — |
| D-Fructose (carbonyl compound according to the invention) | — | 0.5 | — |

-continued

| | EXAMPLE | | |
|---|---|---|---|
| | 11 | 12 | 13 |
| Maleic acid (carbonyl compound according to the invention) | — | — | 0.5 |
| Common dye support | () | () | (**) |
| Demineralized water qs | 100 g | 100 g | 100 g |

(**) common dye support: identical to that of Examples 1 to 10.

At the time of use, each dye composition above was mixed with an equal amount by weight of an oxidizing composition consisting of a 20-volumes aqueous hydrogen peroxide solution (6% by weight).

Each resulting composition was applied for 30 minutes to locks of natural grey hair containing 90% white hairs. The locks of hair were then rinsed, washed with a standard shampoo and then dried.

In the three cases, a strong and resistant shade, with good harmlessness, is obtained.

The invention claimed is:

1. A composition for the oxidation dyeing of human keratin fibers, and in particular of human keratin fibers such as the hair, comprising:
    a medium that is suitable for dyeing
    at least one oxidation base comprising 4,5-diamino 1-hydroxyethyl pyrazole,
    at least one carbonyl compound selected from the group consisting of polyimides and compounds of formulae (I), (II) and (III)

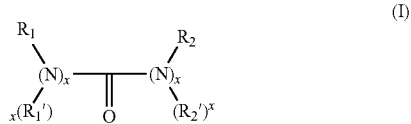

wherein
    R1, R1', R2 and R2' denote, independently of each other, a hydrogen atom; a saturated or unsaturated aliphatic hydrocarbon-based chain containing from 1 to 30 carbon atoms, which may be interrupted with one or more hetero atoms or with one or more carbonyl groups, which is unsubstituted or substituted with one or more groups chosen from hydroxyl, $C_1$-$C_4$ alkoxy, amino, carboxyl, $C_1$-$C_{10}$ alkoxycarbonyl, halogen, nitro, mono- or di($C_1$-$C_4$)alkylamino, mono- or dihydroxy($C_1$-$C_4$)alkylamino or $C_6$-$C_{20}$ aryl groups; a $C_6$-$C_{20}$ aryl group, which is unsubstituted or substituted with one or more groups chosen from hydroxyl, amino, nitro, halogen, carboxyl, ($C_1$-$C_{10}$)alkoxycarbonyl, $C_1$-$C_4$ alkyl, mono- or polyhydroxy($C_1$-$C_4$)alkyl, $C_1$-$C_4$ alkoxy, mono- or di($C_1$-$C_4$) alkylamino or mono- or dihydroxy($C_1$-$C_4$)alkylamino groups,
    x denotes 0, and $R_1$ and $R_2$ can form, together with the C=O group, a saturated ring optionally fused to one or more benzene nuclei that may be substituted with one or more $C_1$-$C_{10}$ alkyl, $C_1$-$C_{10}$ alkoxy, carboxyl or $C_1$-$C_{10}$ alkoxycarbonyl radicals,

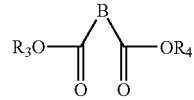

wherein
    B denotes a saturated or unsaturated aliphatic hydrocarbon-based chain containing from 1 to 30 carbon atoms, which may be interrupted with one or more hetero atoms or with one or more carbonyl groups, which is unsubstituted or substituted with one or more groups chosen from hydroxyl, $C_1$-$C_4$ alkoxy, amino, carboxyl, $C_1$-$C_{10}$ alkoxycarbonyl, halogen, nitro, mono- or di($C_1$-$C_4$) alkylamino, mono- or dihydroxy ($C_1$-$C_4$)alkylamino or $C_6$-$C_{20}$ aryl groups; a $C_6$-$C_{20}$ aryl group, which is unsubstituted or substituted with one or more groups chosen from hydroxyl, amino, nitro, halogen, carboxyl, ($C_1$-$C_{10}$)alkoxycarbonyl, $C_1$-$C_4$ alkyl, mono- or polyhydroxy($C_1$-$C_4$)alkyl, $C_1$-$C_4$ alkoxy, mono- or di($C_1$-$C_4$) alkylamino or mono- or dihydroxy($C_1$-$C_4$)alkylamino groups,
    $R_3$ and $R_4$, which may be identical or different, represent a hydrogen atom, a $C_1$-$C_{10}$ alkyl, $C_1$-$C_{10}$monohydroxyalkyl or $C_2$-$C_{10}$ polyhydroxyalkyl radical, Na, K or $NH_4$,
wherein the at least one carbonyl compound is selected from the group consisting of aldoses and ketoses of formula (I), maleic acid, and a polyimide obtained from pyromellitic dianhydride.

2. The composition of claim 1, wherein said at least one carbonyl compound represents from 0.00001% to 10% by weight approximately relative to the total weight of the dye composition.

3. The composition of claim 1, wherein said 4,5-diamino 1-hydroxyethylpyrazole represents from 0.0005% to 12% by weight relative to the total weight of the dye composition.

4. The composition of claim 3, wherein said 4,5-diamino 1-hydroxyethylpyrazoles represents from 0.005% to 6% by weight relative to the total weight of the dye composition.

5. The composition of claim 1, wherein the weight ratio of said at least one carbonyl compounds to said 4,5-diamino 1-hydroxyethylpyrazole is between 0.001 and 100.

6. The composition of claim 1, further comprising at least one coupler.

7. The composition of claim 6, wherein said at least one coupler represents from 0.0001% to 10% by weight approximately relative to the total weight of the dye composition.

8. The composition of claim 1, further comprising at least one additional oxidation base other than said 4,5-diamino 1-hydroxyethyl pyrazole.

9. The composition of claim 8, wherein said at least one additional oxidation base represents from 0.0005% to 12% by weight approximately relative to the total weight of the dye composition.

10. The composition of claim 1, wherein said composition has a pH of between 3 and 12.

11. The composition of claim 1, wherein said composition is in the form of liquids, creams or gels or in any other form that is suitable for dyeing keratin fibres, and especially human hair.

12. The composition of claim 2, wherein said carbonyl compound(s) represent(s) from 0.001% to 5% by weight approximately relative to the total weight of the dye composition.

13. The composition of claim 12, wherein said carbonyl compound(s) represent(s) from 0.001% to 3% by weight approximately relative to the total weight of the dye composition.

14. The composition of claim 7, wherein said at least one coupler represents from 0.005% to 5% by weight approximately relative to the total weight of the dye composition.

15. The composition of claim 5, wherein the weight ratio of said at least one carbonyl compound to said 4,5-diamino 1-hydroxyethyl pyrazole is between 0.01 and 10.

16. The composition of claim 1, wherein the at least one carbonyl compound is selected from the group consisting of fructose, maleic acid, and a polyimide obtained from pyromellitic dianhydride or benzophenone dianhydride.

17. A composition for the oxidation dyeing of human keratin fibers, and in particular of human keratin fibers such as the hair, comprising:
a medium that is suitable for dyeing
at least one oxidation base comprising 4,5-diamino 1-hydroxyethyl pyrazole,
at least one carbonyl compound selected from the group consisting of polyimides and compounds of formulae (I), (II) and (III)

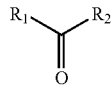

wherein
R1 and R2 denote, independently of each other, a hydrogen atom; a saturated or unsaturated aliphatic hydrocarbon-based chain containing from 1 to 30 carbon atoms, which may be interrupted with one or more hetero atoms or with one or more carbonyl groups, which is unsubstituted or substituted with one or more groups chosen from hydroxyl, $C_1$-$C_4$ alkoxy, amino, carboxyl, $C_1$-$C_{10}$ alkoxycarbonyl, halogen, nitro, mono- or di($C_1$-$C_4$) alkylamino, mono- or dihydroxy($C_1$-$C_4$)alkylamino or $C_6$-$C_{20}$ aryl groups; a $C_6$-$C_{20}$ aryl group, which is unsubstituted or substituted with one or more groups chosen from hydroxyl, amino, nitro, halogen, carboxyl, ($C_1$-$C_{10}$) alkoxycarbonyl, $C_1$-$C_4$ alkyl, mono- or polyhydroxy($C_1$-$C_4$)alkyl, $C_1$-$C_4$ alkoxy, mono- or di($C_1$-$C_4$) alkylamino or mono- or dihydroxy($C_1$-$C_4$)alkylamino groups,
x denotes 0, and $R_1$ and $R_2$ can form, together with the C=O group, a saturated ring optionally fused to one or more benzene nuclei that may be substituted with one or more $C_1$-$C_{10}$ alkyl, $C_1$-$C_{10}$ alkoxy, carboxyl or $C_1$-$C_{10}$ alkoxycarbonyl radicals,

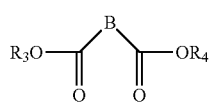

-continued

wherein
B denotes a saturated or unsaturated aliphatic hydrocarbon-based chain containing from 1 to 30 carbon atoms, which may be interrupted with one or more hetero atoms or with one or more carbonyl groups, which is unsubstituted or substituted with one or more groups chosen from hydroxyl, $C_1$-$C_4$ alkoxy, amino, carboxyl, $C_1$-$C_{10}$ alkoxycarbonyl, halogen, nitro, mono- or di($C_1$-$C_4$) alkylamino, mono- or dihydroxy ($C_1$-$C_4$)alkylamino or $C_6$-$C_{20}$ aryl groups; a $C_6$-$C_{20}$ aryl group, which is unsubstituted or substituted with one or more groups chosen from hydroxyl, amino, nitro, halogen, carboxyl, ($C_1$-$C_{10}$)alkoxycarbonyl, $C_1$-$C_4$ alkyl, mono- or polyhydroxy($C_1$-$C_4$)alkyl, $C_1$-$C_4$ alkoxy, mono- or di($C_1$-$C_4$) alkylamino or mono- or dihydroxy($C_1$-$C_4$)alkylamino groups,
$R_3$ and $R_4$, which may be identical or different, represent a hydrogen atom, a $C_1$-$C_{10}$ alkyl, $C_1$-$C_{10}$ monohydroxyalkyl or $C_2$-$C_{10}$ polyhydroxyalkyl radical, Na, K or $NH_4$;
wherein the at least one carbonyl compound is selected from the group consisting of aldoses and ketoses of formula (I), maleic acid, and a polyimide obtained from pyromellitic dianhydride; and
wherein the composition is free from any volatile or non-volatile silicone.

18. The composition of claim 17, wherein the at least one carbonyl compound is selected from the group consisting of fructose, maleic acid, and a polyimide obtained from pyromellitic dianhydride.

19. A process for dyeing keratin fibres, and in particular human keratin fibres such as the hair, comprising the steps of applying the composition of claim 1 to said keratin fibres and applying an oxidizing agent to said keratin fibers to reveal the color wherein said color is revealed at acidic, neutral or alkaline pH.

20. The process of claim 19, wherein said oxidizing agent is selected from the group consisting of hydrogen peroxide, urea peroxide, alkali metal bromates, persalts such as perborates, percarbonates and persulphates, and peracids.

21. A process for dyeing keratin fibres, and in particular human keratin fibres such as the hair, comprising the steps of applying a composition containing at least one carbonyl compound as defined in claim 1 to said keratin fibres in a first stage, applying a composition containing at least one diaminopyrazole as defined in claim 1 to said keratin fibers in a second stage, developing the color with an oxidizing agent and optionally rinsing the keratin fibers either before or after the application of the oxidizing agent.

22. A multi-compartment device comprising a first compartment containing said composition for the oxidation dyeing of human keratin fibers of claim 1 and a second compartment containing an oxidizing composition.

23. A multi-compartment device comprising a first compartment containing said carbonyl compound of claim 1, a second compartment containing said 4-5-diamino 1-hydroxyethyl pyrazole of claim 1, and a third compartment containing an oxidizing composition.

* * * * *

UNITED STATES PATENT AND TRADEMARK OFFICE
CERTIFICATE OF CORRECTION

| | | |
|---|---|---|
| PATENT NO. | : 7,951,209 B2 | Page 1 of 1 |
| APPLICATION NO. | : 11/975995 | |
| DATED | : May 31, 2011 | |
| INVENTOR(S) | : Jean Cotteret | |

It is certified that error appears in the above-identified patent and that said Letters Patent is hereby corrected as shown below:

Column 1, after the title, insert -- This application is a continuation of U.S. Appl. No. 10/451,553, filed December 18, 2003, abandoned; said 10/451,553 is a 371 National Stage Entry of Appl. No. PCT/FR01/03729, filed November 26, 2001. This application also claims priority benefit of French Appl. No. FR 00/16952, filed December 22, 2000. --.

Column 18, line 48, "compounds" should read -- compound --.

Column 19, line 19, delete "or benzophenone dianhydride".

Signed and Sealed this
Fourth Day of December, 2012

David J. Kappos
*Director of the United States Patent and Trademark Office*